US008892217B2

(12) United States Patent
Camps et al.

(10) Patent No.: US 8,892,217 B2
(45) Date of Patent: Nov. 18, 2014

(54) IMPLANTABLE MEDICAL LEAD WITH PROXIMAL RETRIEVAL WIRE

(75) Inventors: Antoine Camps, Gulpen-Wittem (NL); Daniel J. Stetson, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 1349 days.

(21) Appl. No.: 11/498,991

(22) Filed: Aug. 3, 2006

(65) Prior Publication Data

US 2008/0046062 A1 Feb. 21, 2008

(51) Int. Cl.
*A61N 1/05* (2006.01)

(52) U.S. Cl.
CPC ................ *A61N 1/05* (2013.01); *A61N 1/0587* (2013.01)
USPC .............................. 607/133; 607/40; 607/116

(58) Field of Classification Search
CPC .... A61N 1/0587; A61N 1/059; A61N 1/0595
USPC ................ 600/373–375, 377–378, 382–383, 600/393–394; 607/115–119, 122, 124, 129, 607/132, 133, 138, 40, 41
See application file for complete search history.

(56) References Cited

U.S. PATENT DOCUMENTS 4,444,207 A 4/1984 Robicsek
4,530,368 A * 7/1985 Saulson et al. ................ 607/132
4,951,687 A * 8/1990 Ufford et al. ................ 607/122
5,314,463 A 5/1994 Camps et al.
5,324,323 A * 6/1994 Bui .............................. 607/119
5,449,381 A * 9/1995 Imran .......................... 607/122
5,792,217 A * 8/1998 Camps et al. ................ 607/119
6,292,704 B1 * 9/2001 Malonek et al. .............. 607/121
6,397,108 B1 5/2002 Camps et al.
6,516,230 B2 * 2/2003 Williams et al. .............. 607/116
2002/0103521 A1 * 8/2002 Swoyer et al. ................ 607/116
2003/0028232 A1 * 2/2003 Camps et al. ................ 607/122
2003/0125787 A1 * 7/2003 Shchervinsky ............... 607/132
2003/0195600 A1 10/2003 Tronnes et al.
2003/0204231 A1 * 10/2003 Hine et al. .................... 607/122

(Continued)

FOREIGN PATENT DOCUMENTS

WO WO 00/71199 11/2000

OTHER PUBLICATIONS

Notification of Transmittal of the International Search Report and the Written Opinion for corresponding PCT Application PCT/US2007/075142 dated Dec. 11, 2007 (16 pgs.).

(Continued)

*Primary Examiner* — Carl H Layno
*Assistant Examiner* — Jennifer Ghand
(74) *Attorney, Agent, or Firm* — Shumaker & Sieffert, P.A.

(57) ABSTRACT

The disclosure describes a medical lead with a retrieval wire that extends from the proximal end of the lead. The retrieval wire allows a physician to insert the medical lead into a patient and grab the retrieval wire to pull the proximal end of the lead away from the implant site. Upon gaining access to a lead connector on the proximal end of the medical lead, the physician may remove the retrieval wire and couple the lead connector to an implantable medical device that provides stimulation therapy. In this manner the physician may avoid damaging the lead connector when retrieving the medical lead. In addition, the retrieval wire may be used to provide test stimulation to verify correct electrode location. The medical lead may be used to stimulate tissue such as the stomach, small intestine, and the large intestine.

31 Claims, 9 Drawing Sheets

14
16
38
34
36
32
18
30
28A
28B
40
16
20

(56) References Cited

U.S. PATENT DOCUMENTS

2003/0220678 A1 11/2003 Tronnes et al.
2005/0033394 A1* 2/2005 Seifert et al. .................. 607/125
2005/0137674 A1* 6/2005 Coe et al. ...................... 607/130
2006/0106445 A1* 5/2006 Woollett ....................... 607/122
2006/0293741 A1* 12/2006 Johnson et al. .............. 623/1.11
2007/0123966 A1* 5/2007 Rieders ......................... 607/122

OTHER PUBLICATIONS

Implantable Gastric Stimulation (IGS™) Lead, Model 9107, Physician's Manual by Transneuronix, Inc. (10 pages) 1991.

* cited by examiner

IMPLANTABLE MEDICAL LEAD WITH PROXIMAL RETRIEVAL WIRE

TECHNICAL FIELD

The invention relates to implantable medical devices and, more particularly, implantable medical leads.

BACKGROUND

Implantable medical leads are used to transmit stimulation therapy energy from a stimulator to target tissue. The medical lead includes one or more electrodes located near a distal end of the lead, a connector disposed at a proximal end of the lead, and one or more conductors traveling the length of the lead to couple the electrodes to corresponding contacts in the connector. An insulating lead body covers the conductive wire to prevent unwanted tissue stimulation. A medical lead allows a stimulator to be implanted at a location remote from the target tissue or outside of the patient while retaining the ability to stimulate the target tissue via the lead.

A medical lead may be implanted by a physician through a process of tunneling the lead through tissue or guiding the lead through blood vessels. The physician continues guiding the lead until the electrodes are disposed adjacent to or within the target tissue. Once the lead is in place, the physician retrieves the proximal end of the lead and couples the connector to the stimulator. Medical leads may be implanted for a variety of stimulation applications, including cardiac stimulation, spinal cord stimulation, gastric stimulation, peripheral nerve stimulation, and other types of electrical stimulation therapy.

As an example, gastric stimulation may require implantation of one or more medical leads implanted to deliver stimulation to relieve gastroparesis, obesity, nausea or other diseases or disorders. After tunneling the medical lead such that one or more electrodes at the distal end of the lead are embedded within the stomach wall, a surgeon typically uses a small forceps or other grasping device to locate the proximal end of the lead and grasp the proximal end. The surgeon then pulls on the proximal end of the lead to access the connector and couple the connector to the simulator. Once implantation is completed, the stimulator may be used to provide gastric stimulation therapy to the patient.

SUMMARY

The disclosure describes an implantable medical lead with a retrieval wire that extends from the proximal end of the lead. The retrieval wire allows a physician to insert the medical lead into a patient and grab the retrieval wire to pull the proximal end of the lead away from the implant site. Upon gaining access to a lead connector on the proximal end of the medical lead, the physician may remove the retrieval wire and couple the lead connector to a medical device that provides stimulation therapy. The medical device may be an implantable electrical stimulator or external electrical stimulator.

One problem that physicians may encounter with conventional medical leads is related to retrieving the proximal end of the lead after the electrodes are implanted. The physician may grasp the connector of the lead or another component of the lead to secure the proximal end of the lead. The force exerted on the proximal end of the lead may damage the connector, compromising lead reliability. Incorporation of a retrieval wire, in accordance with this disclosure, eliminates the need to grasp the proximal end of the lead, and can avoid or reduce lead damage due to the retrieval process.

In some embodiments, in addition to its use in retrieval, the retrieval wire may be coupled to one or more electrodes at the distal end of the lead. In this case, the retrieval wire may be electrically conductive, and may be used to deliver test stimulation from an external test stimulator to verify correct electrode location. The external test stimulator may deliver test pulses to one or more electrodes of the lead such that the physician may verify correct placement of the electrodes.

In one embodiment, the invention provides a medical lead comprising a flexible lead body having a distal end and a proximal end, one or more electrodes disposed near the distal end of the lead body, and a retrieval wire that extends from the proximal end of the lead body.

In another embodiment, the invention provides a method for implanting a medical lead in a patient, the method comprising inserting a distal end of a medical lead into a patient, positioning one or more electrodes of the medical lead adjacent to a target tissue of the patient, and pulling a retrieval wire that extends from a proximal end of the medical lead to access the proximal end of the medical lead.

In an additional embodiment, the invention provides an implantable gastric lead for stimulating a patient, the lead comprising a flexible lead body having a distal end and a proximal end, one or more electrodes disposed near the distal end of the flexible lead body, and a retrieval wire that extends along substantially an entire length of the flexible lead body and extends out from the proximal end of the lead body, wherein the retrieval wire is constructed of a polypropylene filament.

In a further embodiment, the invention provides an implantable stimulation system comprising an electrical stimulator, and an implantable lead coupled to the electrical stimulator, wherein the lead includes a flexible lead body having a distal end and a proximal end, one or more electrodes disposed near the distal end of the lead body, and a retrieval wire that extends from the proximal end of the lead body and is detachable from the lead body upon coupling of the lead to the electrical stimulator.

In various embodiments, the invention may provide one or more advantages. For example, the addition of a retrieval wire to a medical lead may allow a physician to retrieve an implanted lead without grasping and damaging a connector on the proximal end of the medical lead. The retrieval wire is securely attached within the lead to prevent unwanted detachment of the retrieval wire from the lead. In addition, the retrieval wire may be configured to deliver test stimulation from an external test stimulator to one or more electrodes. When no longer needed, the retrieval wire may be cut from the lead and discarded.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
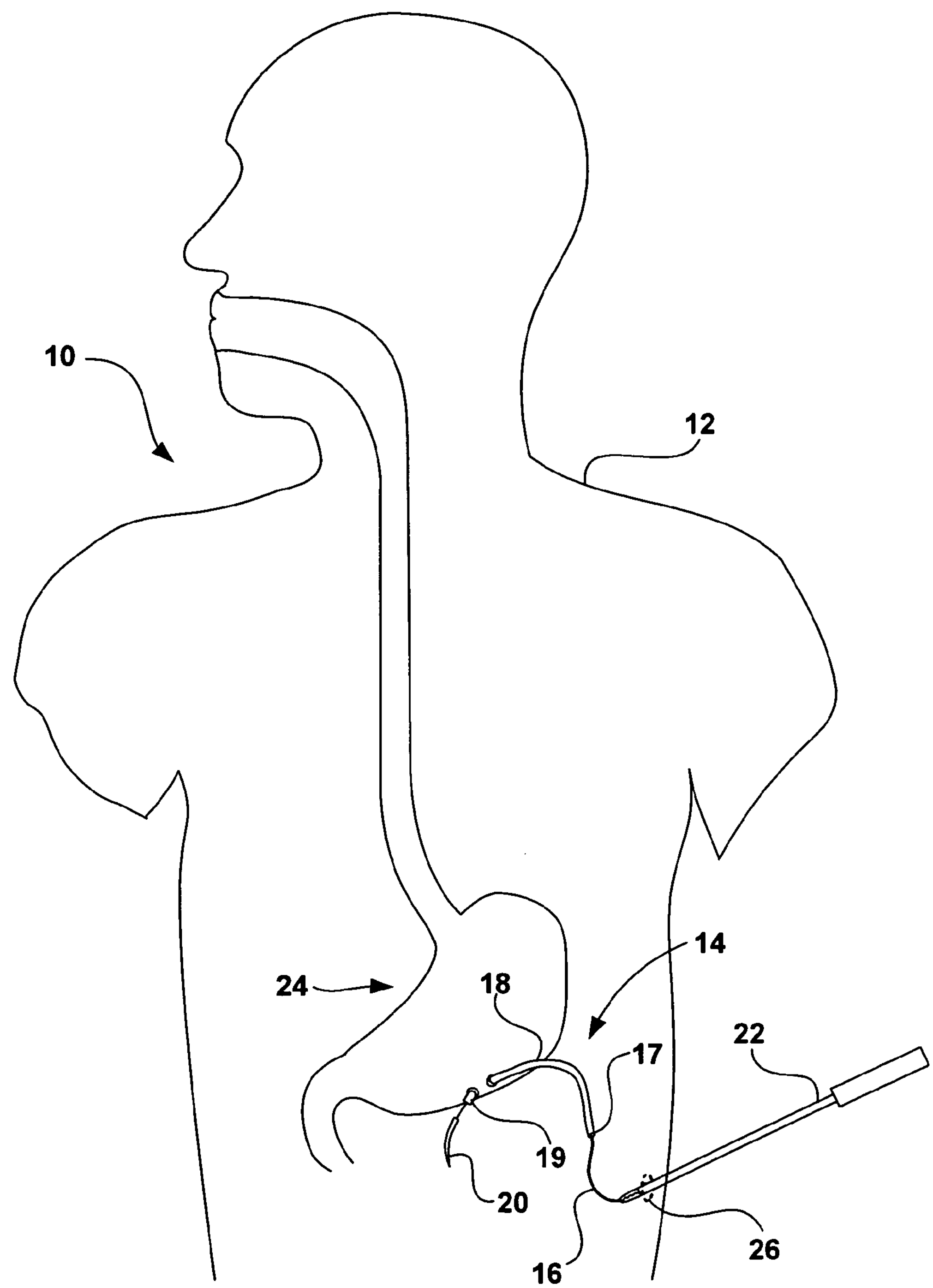
FIG. 1 is a schematic diagram illustrating an implantable medical lead that includes a retrieval wire that aids in lead implantation and retrieval.

The disclosure is directed to a medical lead with a retrieval wire extended from the proximal end of the medical lead. The retrieval wire is available to the physician during implantation to retrieve the proximal end of the medical lead after the lead has been tunneled to the implantation site. The physician may grasp the retrieval wire with forceps without the possibility of damaging a functional component of the medical lead, such as lead connector contacts. Once the proximal end of the lead has been accessed, the retrieval wire may be removed and the connector of the lead may be coupled to an electrical stimulator.

Without a retrieval wire, physicians may encounter the problem of damaged leads after the lead is retrieved from the patient. When the physician grasps the connector of the lead or another component of the lead, a large contact force may cause structural damage to the lead or surface modification to the connector. These damaging forces may be caused due to a lack of tactile feedback afforded to the physician through the use of grasping tools, such as a forceps commonly used during a laparoscopic or laparotomy procedure. These changes may compromise lead integrity, reliability, and functionality. Therefore, a retrieval wire may eliminate these problems associated with implanting a medical lead.

The retrieval wire may be a continuous wire disposed throughout the entire length of the medical lead and extended out from the proximal end of the lead. Other embodiments of the medical lead may include a retrieval wire that is only attached within or to the proximal end of the lead. The retrieval wire may be electrically non-conductive or electrically conductive, and an electrically conductive wire may be used to provide test pulses to verify correct electrode placement. In any case, the retrieval wire may be removed from the lead before coupling the connector to the electrical stimulator, e.g., by cutting or otherwise detaching the retrieval wire.

The term "wire," as used herein, may refer to any of a variety of elongated filament-like members, including members constructed from electrically conductive, metallic materials or from electrically non-conductive, non-metallic materials, or from a combination of such materials, e.g., an electrically conductive core with an electrically nonconductive cover or coating. The retrieval wire may be substantially flexible or substantially rigid. The length of the retrieval wire may vary according to the particular application, implantation environment, patient size, and/or surgical preference.

While the disclosure is generally directed to gastric stimulation therapy and related medical lead implantation, the medical lead described herein may be used for other non-gastric applications. For example, a medical lead with a retrieval wire may be utilized in cardiac stimulation, spinal cord stimulation, peripheral nerve stimulation, pelvic floor stimulation, muscle stimulation, or any other stimulation therapy that requires a medical lead. In addition, the disclosure is not limited to the type of medical lead described herein and the associated retrieval wire. The retrieval wire may be included in any type of lead, such as cylindrical leads, paddle leads, conformable leads, unipolar leads, bipolar leads, or leads with any other type of electrode configuration.

FIG. 1 is a schematic diagram illustrating a patient 12 and an implantable medical lead 14 that includes a retrieval wire that aids in implantation. As shown in FIG. 1, system 10 includes medical lead 14 (lead 14), stomach 24, and forceps 22. Lead 14 includes retrieval wire 16, flexible lead body 18, and needle 20. Lead 14 is tunneled into patient 12 through a skin opening 26 created by a physician, e.g., using laparoscopic techniques. The physician uses forceps 22 to grasp retrieval wire 16 and pull the proximal end of lead body 18 away from stomach 24 and toward the location of an implantable medical device (IMD) (not shown). The IMD may be implanted in a subcutaneous pocket in the abdomen of the patient.

Lead 14 includes a proximal end 17 and distal end 19, where needle 20 is at the distal end and retrieval wire 16 is the proximal end. Needle 20 is attached to the distal end of flexible lead body 18 while retrieval wire 16 extends from the proximal end of the lead body. Lead body 18 may have a variety of forms. For example, lead body 18 may include a flexible, electrically insulative cover or coating that contains one or more conductors, e.g., in an axial or coiled single-filar or multi-filar configuration. One or more electrodes (not shown) are disposed on the distal end of flexible lead body 18 to deliver bipolar stimulation to the wall of stomach 24. Retrieval wire 16 extends from a channel within flexible lead body 18. In this manner, retrieval wire 16 does not increase the diameter of flexible lead body 18 to reduce tissue displacement during insertion of lead 14. Retrieval wire 16 may be a continuous filament that is disposed throughout the entire length of flexible lead body 18 and crimped at one or more location along the length of lead body 18. The continuous filament may attach to needle 20. In other embodiments, retrieval wire 16 may be attached within a proximal section of flexible lead body 18, such that the wire is not a continuous filament disposed throughout the length of lead 14.

The physician begins implantation of lead 14 by creating skin opening 26 at a predetermined location of patient 12. Skin opening 26 may be created to a size that accepts the passage of lead 14 and forceps 22. While skin opening 26 is shown in FIG. 1 near the upper abdomen or chest of patient 12, the skin opening may be created at any location which provides adequate access to the portion of stomach 24 to be stimulated. Other locations for skin opening 26 may include the lower abdomen, lower back, navel, upper pelvis. Skin opening 26 may correspond to the location that an IMD may be ultimately located.

Once skin opening 26 is created, the physician may insert lead 14 through the opening and tunnel the lead through patient 12 in order to approach the target tissue of stomach 24. An endoscopic camera may be used to facilitate guidance of the lead through patient 12. The physician pierces the wall of stomach 24 with needle 20 and exits the stomach wall before breaching the inner lining of the stomach. The physician then pulls the distal end of lead body 18 through the wall of stomach 24 until the electrode or electrodes of lead 14 are positioned within the target tissue of stomach 24. The target tissue of stomach 24 may be smooth muscle that is involved with peristaltic movement of the stomach.

After lead 14 is correctly positioned, the physician may use one or more sutures or anchors to attach the lead to stomach 24 or other adjacent tissue and remove needle 20 from the lead. At this point in the implantation procedure, the physician must retrieve the proximal end of lead 14 to couple the connector to the IMD. The physician uses forceps 22 to reach into patient 12 and grasp retrieval wire 16. The physician pulls on retrieval wire 16 with forceps 22 to gain access to the connector. Once the physician has obtained the connector located on the proximal end of lead body 18, the physician removes retrieval wire 16 and couples the connector to the IMD. Electrical contacts on the connector are coupled to conductors that extend through lead body to electrodes at distal end 19. Hence, the IMD can be coupled to the distal electrodes via the electrical contacts on the connector and the conductors in lead body 18.

The physician may remove retrieval wire 16 by cutting the wire next to the proximal end of flexible lead body 18. Other methods of removing retrieval wire 16 may include melting the wire, fracturing the wire, crimping the wire, or any other manner of removing the wire without disturbing the already implanted lead 14. Retrieval wire 16 may be substantially axially stiff to prevent substantial distention of the wire when tensile forces are applied to the wire.

Forceps 22 may be any type of forceps that may be accepted within skin opening 26. Forceps 22 may include minimally invasive forceps, knot tying devices, or any type of device with an elongated nose and small jaw for grasping retrieval wire 16. Forceps 22 may include a locking mechanism or require constant force from the physician to retain wire 16. In some embodiments, forceps 22 may be specialized for reaching retrieval wire 16 by having a certain curvature to navigate through patient 12 tissue.

After retrieval wire 16 is removed from flexible lead body 18, the connector may couple lead 14 to an IMD (e.g., implantable stimulator) or external chronic or trial stimulator. The IMD may be implanted into a subcutaneous pocket created within patient 12. The external trial stimulator may provide temporary stimulation therapy to patient 12 in order to evaluate the efficacy of stimulation therapy. If successful, lead 14 may be coupled to an IMD. In some embodiments, a lead extension may be coupled to the connector of lead 14. In alternative embodiments, a laparoscopic technique may be used to implant lead 14 in patient 12 through the use of retrieval wire 16.

Figure 2:
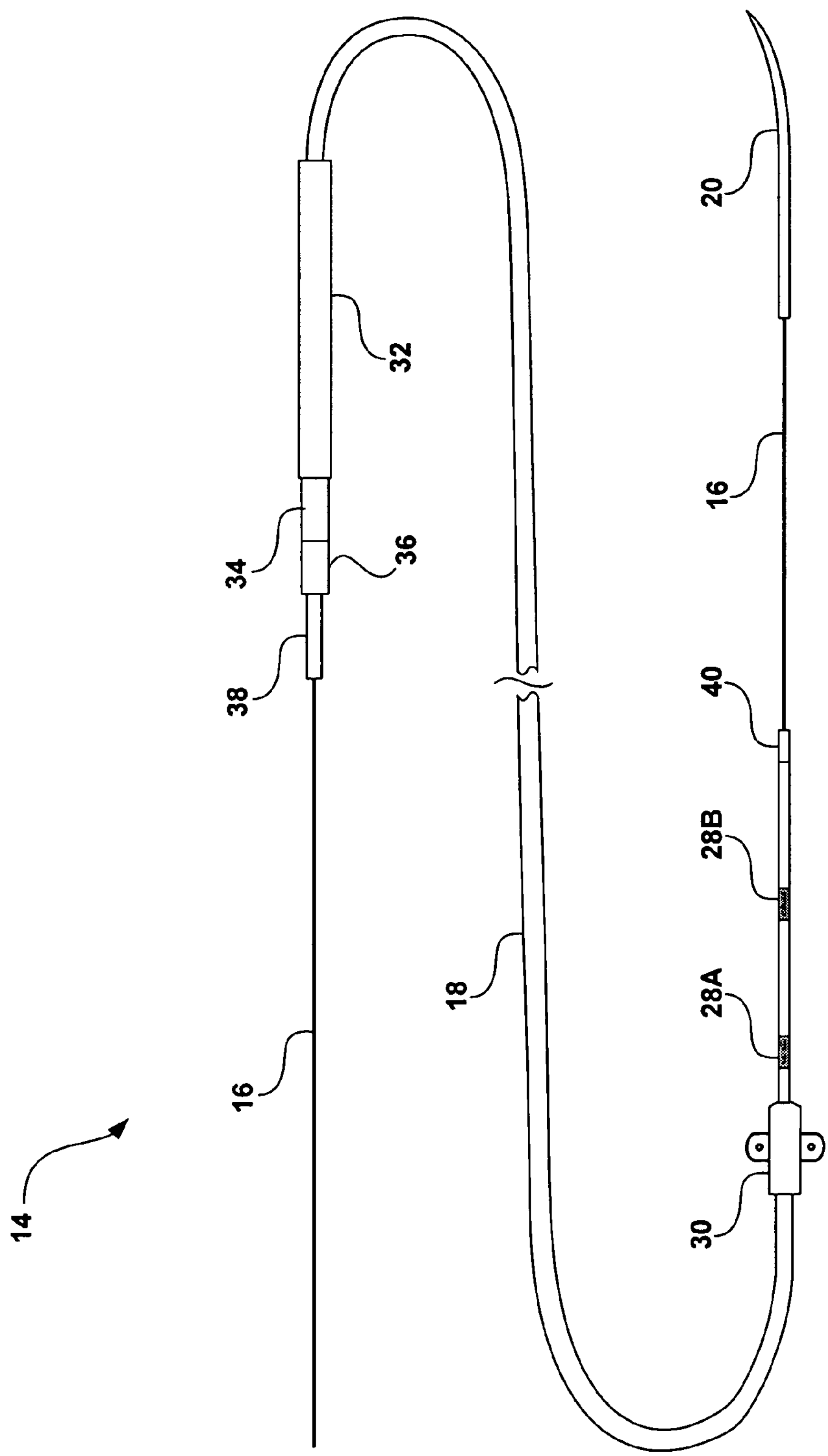
FIG. 2 is a schematic diagram illustrating a side view of an example medical lead with a retrieval wire.

FIG. 2 is a schematic diagram illustrating a side view of an example medical lead with a retrieval wire. As shown in FIG. 2, medical lead 14 includes retrieval wire 16, needle 20, distal cap 40, electrodes 28A and 28B, and attachment device 30. Lead 14 also includes lead body 18, boot 32, connector ring 34, assembly 36, and connector 38. The components of lead 14 allow electrical stimulation pulse signals to be transmitted from an IMD to target tissue in stomach 24. In some cases, electrical signals indicative of physiological conditions also may be transmitted from electrodes to an IMD for sensing purposes. As illustrated by FIG. 2, flexible lead body 18 is flexible laterally to weave through tissue of patient 12. However, flexible lead body 18 and retrieval wire 16 may be axially stiff to resist length changes and torsionally stiff to limit twist within lead 14. In some embodiments, retrieval wire 16 may provide the majority of axial strength within lead 14.

Needle 20 is used to pierce a hole in the wall of patient 12 stomach so that electrodes 28A and 28B (collectively "electrodes 28) can be pulled into place within stomach muscle. Needle 20 is attached to retrieval wire 16, and the retrieval wire may be cut to remove the needle once electrodes 28 are implanted. Retrieval wire 16 is attached to distal connector 40 near electrode 28B. Electrodes 28 are positioned along lead 14 according to the stimulation to be delivered to stomach 24. Attachment device 30 is attached to the wall of stomach 24 with suture, staples, or other mechanism to prevent electrodes 28 from migrating within the stomach wall.

Extending from attachment device 30 is lead body 18 which is a flexible insulating cover for retaining wire 16 and coiled conductors that electrically couple electrodes 28 to corresponding connector ring 34 and 38. Lead body 18 may be constructed of a biocompatible polymer such as silicone, polypropylene, polyurethane, or other material. Lead body 18 is fitted within boot 32, and the lead body and boot are connected to connector ring 34. Connector ring 34 is separated from connector 38 with assembly 36. Connector ring 34 and connector 38 are electrically coupled to an IMD such that electrodes 28 may deliver stimulation pulses to stomach 24. For example, connector ring 34 and connector 38 are electrically coupled to respective electrodes 28A, 28B via electrical conductors that extend along the length of lead body 18. Connector ring 34 and connector 38 form electrical contacts for connection to the IMD.

In an exemplary embodiment, retrieval wire 16 is disposed as a continuous wire throughout the entire length of lead 14. Retrieval wire 16 may be crimped or clamped at one or more locations along lead 14, such that other lead elements remain at their fixed locations. In some embodiments, retrieval wire 16 may include multiple sections within lead 14 that together create the retrieval wire that runs the entire length of the lead. In alternative embodiments, retrieval wire 16 may only be disposed at the proximal end of lead 14, such that the wire is attached to the proximal end of the lead. In any event, retrieval wire 16 is removed from lead 14 before connecting the wire to an IMD.

Retrieval wire 16 may be constructed of one or more filaments of a flexible material that retains substantial axial rigidity. The filaments may be constructed of polypropylene, but other materials may be used. For example, polymers such as polyurethane, polyethylene, expanded polytetrafluoroethylene, or nylon may be constructed as a single filament, multifilament, or braided structure to create retrieval wire 16. Other materials to construct retrieval wire 16 may include steel, stainless steel, aluminum, titanium, or metallic alloys. Also, combinations of polymeric and metallic materials may be used to construct wire 16. In some embodiments, retrieval wire 16 may be a tube which allows a structure to be inserted within the tube or a fluid to be delivered to patient 12. The fluid may be a sterile fluid or drug to treat patient 12.

The length of lead 14 may be generally between approximately 20 centimeters (cm) and 120 cm and preferably between approximately 50 cm and 90 cm. The length of retrieval wire 16 may be substantially similar to the length of lead 14, without being disposed within needle 20. The section of retrieval wire 16 extending out of connector 38 may be generally between 4 cm and 30 cm and preferably between approximately 8 cm and 16 cm. The diameter of retrieval wire 16 may be generally between approximately 100 micrometers (μm) and 2 millimeters (mm) and preferably between approximately 200 μm and 500 μm.

As mentioned previously, retrieval wire 16 may be axially stiff. Axial stiffness prevents failure of retrieval wire 16 when the physician pulls on the wire to retrieve the proximal end of lead 14. Retrieval wire 16 may allow a small amount of axial elasticity on the order of less than approximately ten percent axial deformation when loaded to near-failure. The failure force of retrieval wire 16 in tension is generally greater than or equal to approximately 2.0 Newtons (N) and preferably greater than or equal to approximately 15.0 N. Accordingly, the strength of a material may vary based upon the diameter of retrieval wire 16. A retrieval wire 16 with a diameter of approximately 300 μm may require a material with a strength greater than approximately 28 megapascals (MPa) to prevent the wire from failure.

Figure 3:
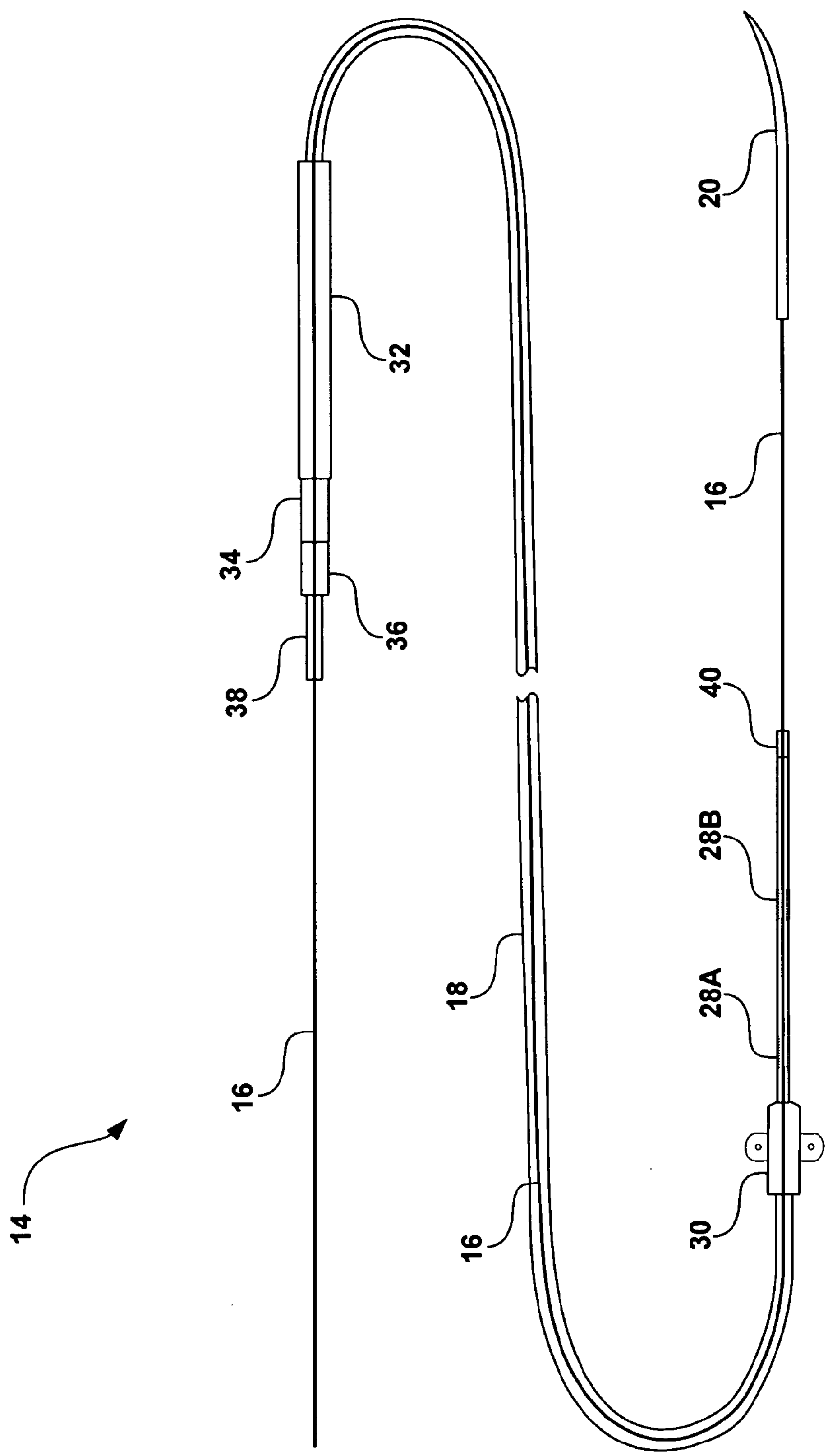
FIG. 3 is a cross-sectional view of an example medical lead with a retrieval wire disposed continuously throughout the length of the lead.

FIG. 3 is a cross-sectional view of an example medical lead with a retrieval wire disposed continuously throughout the length of the lead. FIG. 3 is very similar to FIG. 2, but FIG. 3 is a cross section of medical lead 14 which illustrates retrieval wire 16 as a continuous filament. As shown in FIG. 3, retrieval wire 16 is disposed within each element of lead 14. The proximal end of needle 20 is crimped to retain the distal end of retrieval wire 16. Other possible attachment points for retrieval wire 16 are within distal cap 40 and connector 38, each of which may be crimped to retain the retrieval wire. While retrieval wire 16 is shown to be located through the centerline of lead 14, the wire may be located away from the center of the lead in other embodiments.

Figure 4:
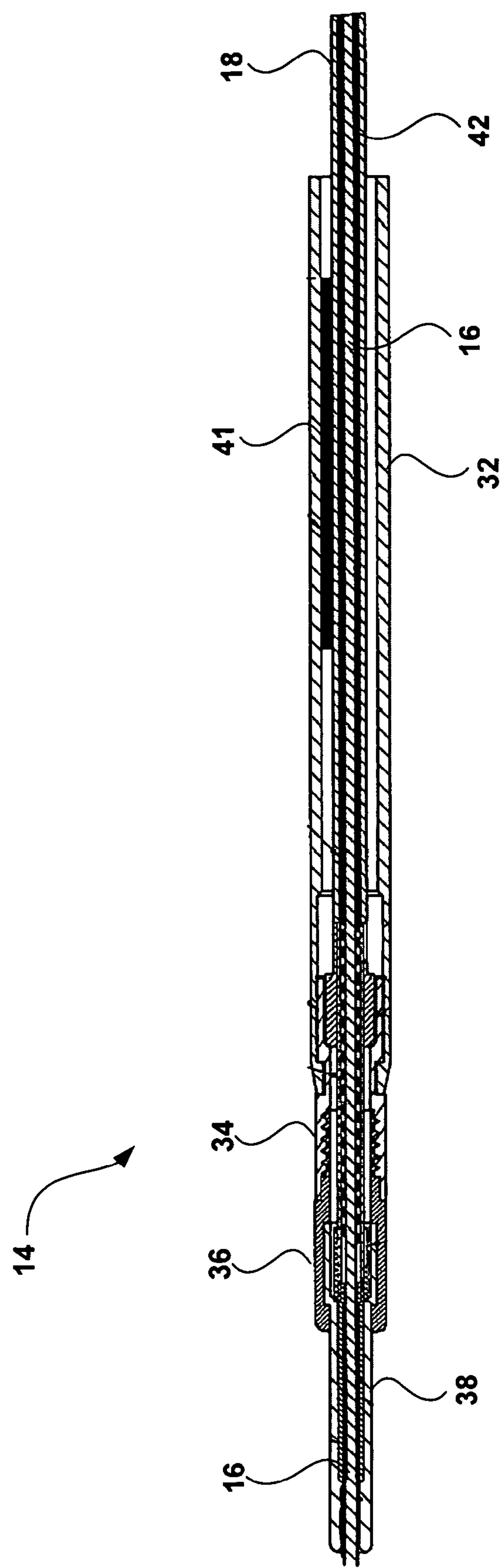
FIG. 4 is a cross-sectional view of the proximal section of an example medical lead with a retrieval wire.

FIG. 4 is a cross-sectional view of the proximal section of an example medical lead with a retrieval wire. As shown in FIG. 4, lead 14 includes retrieval wire 16 throughout the length of the proximal section of the lead. From the proximal side of lead 14, connector 38 fits within assembly 36. Assembly 36 is then attached to connector ring 34. Connector ring 34 is fitted within boot 32 such that the entire proximal section is hermetically sealed from body fluids. Coiled wire 42 includes two or more coiled wires that transmit the stimulation pulses from electrically conductive connector 38 and electrically conductive connector ring 34 to electrodes 28 implanted within stomach 24. Coiled wire 42 includes conductors traveling the length of lead 14 to couple electrodes 28 to corresponding contacts in connector ring 34. Between coiled wires 42 and boot 32 resides a serial number label 41 to identify the specific lead 14.

Connector 38 and connector ring 34 are constructed of electrically conductive metals or metal alloys that contact cylindrical connectors of an IMD. Connector 38 and connector ring 34 do not come into contact with fluids of tissues of patient 12 as boot 32 provides a seal to the IMD. Assembly 36 may be constructed of an electrically insulating polymeric material that isolates connector 38 from connector ring 36. Boot 32 is constructed of a flexible polymeric material such as polyurethane or polyethylene that protects the proximal section of lead 14 and allows coiled wires 42 to bend without permitting small curvatures that could result in a fracture of a wire of the coiled wires.

Each connection between elements of lead 14 may be secured through screwed connections, adhesives, friction fits, or crimping. In any case, the connections must prohibit disassembly of lead 14 during use in patient 12. Coiled wire 42 may be coiled around retrieval wire 16 so that the retrieval wire can provide axial stiffness to the coiled wire. In other embodiments, coiled wire 42 may be coiled adjacent to retrieval wire 16 or within the retrieval wire.

In some embodiments, lead 14 may include more than two electrical contacts or connectors such that a greater number of electrodes 28 can be used to deliver therapy to patient 12. For example, four connectors may be located at the proximal end of lead 14 for insertion into an IMD. The connectors may be complete cylinders similar to connector 38 or connector ring 34, or the connectors may be circumferentially specific such that two or more connectors are located around the circumference of lead 14. In addition, the connectors may be covered in a protective sleeve (not shown) until the physician removes retrieval wire 16 and connects the connectors to the IMD.

Figure 5A:
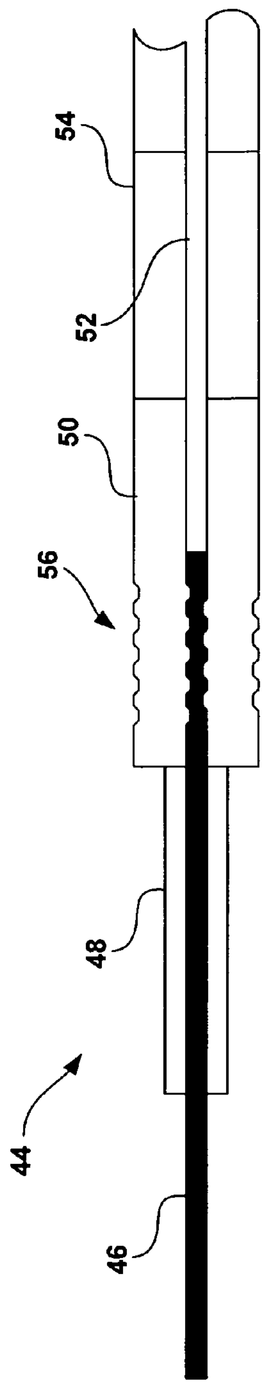
FIGS. 5A, 5B and 5C are cross-sectional side views of example medical leads with retrieval wires attached to a proximal section of the lead.
Figure 5B:
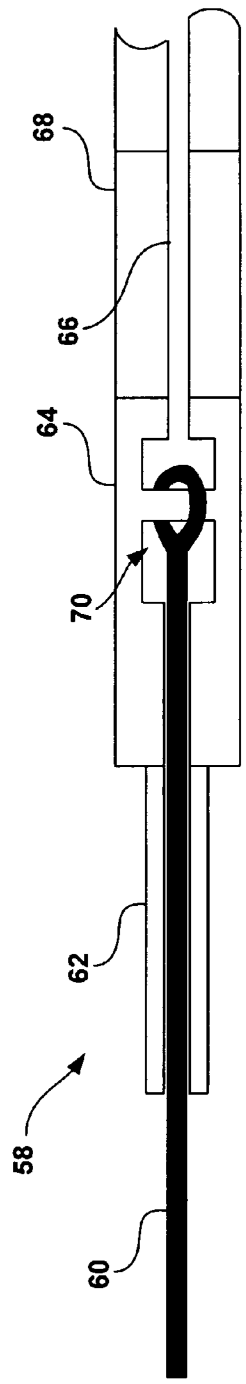
Figure 5C:
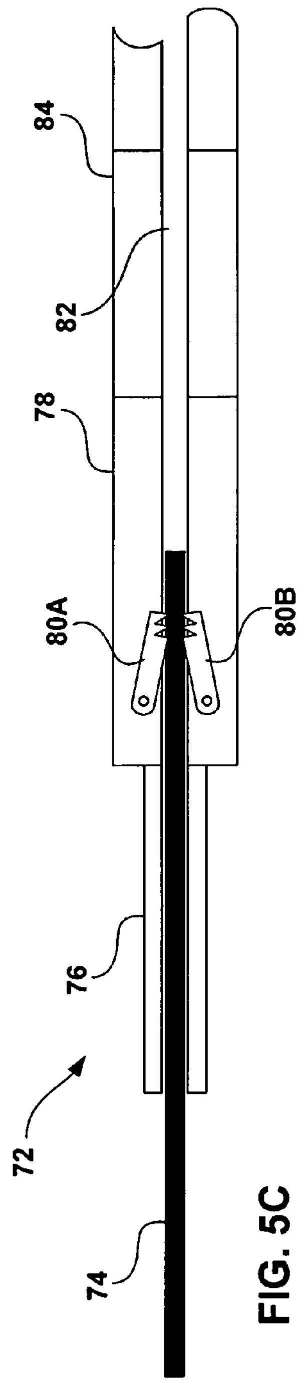

FIGS. 5A, 5B and 5C are cross-sectional side views of example medical leads with retrieval wires attached to a proximal section of the lead. As shown in FIGS. 5A-C, retrieval wires 46, 60 and 74 represent different embodiments of retrieval wire 16, in which retrieval wires 46, 60 and 74 do not continue through the entire length of the respective leads. Instead, each retrieval wire 46, 60, 74 is connected at a proximal end of a respective lead 44, 58, 72. Leads 44, 58 and 72 are embodiments of lead 14 described above.

FIG. 5A illustrates lead 44 with retrieval wire 46 extending out from connector 48 and anchor assembly 50. Anchor assembly 50 is connected to connector ring 54 and forms retrieval wire channel 52. Retrieval wire 48 is placed within channel 52, and the outside of anchor assembly 50 is compressed to produce crimped region 56.

The compressed material of anchor assembly 50 is translated into narrower portions of channel 52 that secure retrieval wire 46 into place. Anchor assembly 50 may be constructed of a malleable material, such as a metal alloy or formable dense polymer. While crimping region 56 includes circumferential oriented crimps, other embodiments may include longitudinal crimps or crimps of some other orientation.

FIG. 5B illustrates lead 58 that includes retrieval wire 60 attached within anchor assembly 64. Anchor assembly 64 is connected to connector ring 68 and forms channel 66. Retrieval wire 60 passes through connector 62 and forms a loop around cross member 70. Retrieval wire 60 may have a preformed loop that is passed through channel 66 and cross member 70 is inserted through the loop of the retrieval wire. In other embodiments, the loop may be formed with a knot at the time of insertion of retrieval wire 60 though a small forceps or other such device. In other embodiments, retrieval wire 60 may be attached within connector 62, closer to the proximal end of lead 58. Alternatively, cross member 70 may be oriented differently within anchor assembly 64 or formed of a different shape than a cylinder.

FIG. 5C illustrates lead 72 that includes retrieval wire 74 attached within anchor assembly 78. Anchor assembly 78 is connected to connector ring 84 and forms channel 82. Retrieval wire 74 extends from connector 76 and passes through clamps 80A and 80B (collectively "clamps 80). Retrieval wire 74 is inserted through channel 82 until the distal end of the retrieval wire pushes clamps 80 away from the channel and the clamps bite into the retrieval wire. In some embodiments, only one clamp, or more than two clamps, may be employed.

Clamps 80 each include a pivot point within anchor assembly 78 and one or more teeth for biting into retrieval wire 74 and securing the retrieval wire within lead 14. A spring or elastic material may provide bias to clamps 80 such that the clamps keep pressure against retrieval wire 74. In this manner, clamps 80 provide a one-way retaining system to easily add retrieval wire 74 to lead 72. In some embodiments, the physician may add retrieval wire 74 only when the retrieval wire is needed for implantation. Alternatively, other one-way retraining systems similar to clamps 80 may be utilized to accept retrieval wire 74 and prevent the retrieval wire to be pulled back out of lead 72.

In each of the embodiments of FIGS. 5A, 5B, and 5C the respective retrieval wire 46, 60, 74 may be completely or partially removed from the proximal end, e.g., by clipping, cutting or otherwise detaching the wire at a point near the proximal end of the lead. The detached retrieval wire 46, 60, 74 may then be discarded. By using retrieval wire 46, 60, 74, however, potential damage to the connector at the proximal end of the lead can be avoided.

Figure 6:
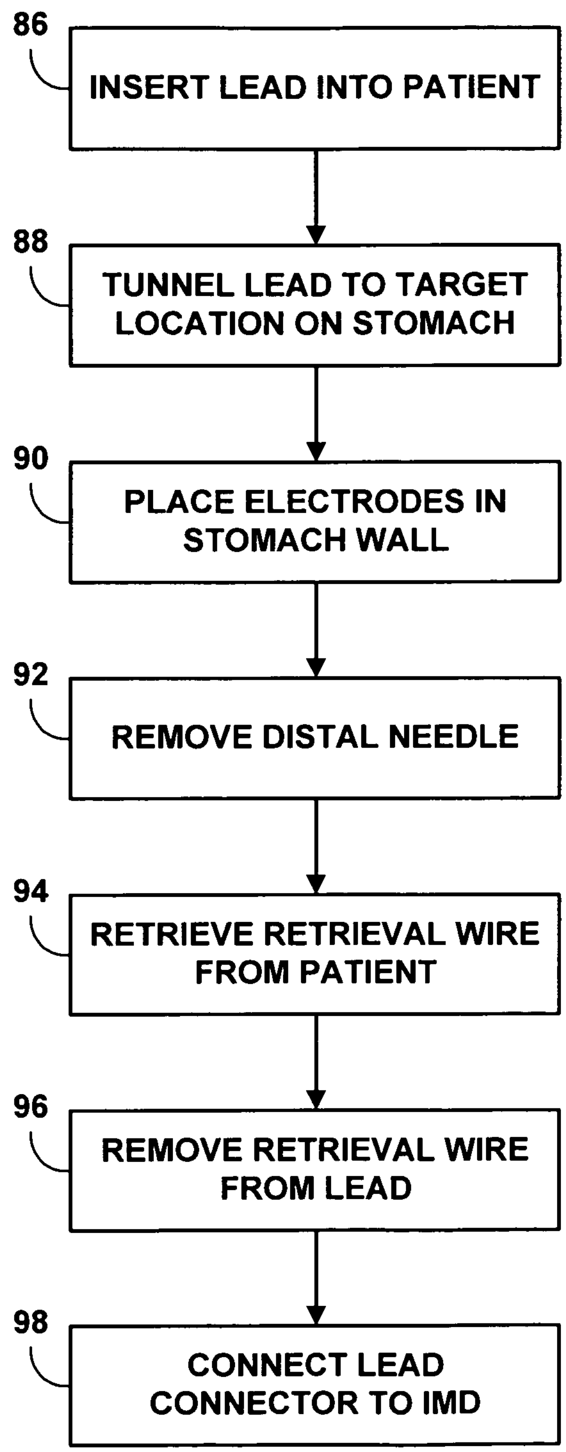
FIG. 6 is a flow chart illustrating a technique for utilizing a retrieval wire during medical lead implantation.

FIG. 6 is a flow chart illustrating a technique for utilizing a retrieval wire during medical lead implantation. As shown in FIG. 6, lead 14 is inserted into a opening 26 created in the skin of patient 12 by a physician (86). Lead 14 is described as an example lead, but any of leads 14, 44, 58 and 72 may be used.

The physician continues by tunneling lead 14 to a target location in the wall of stomach 24 (88). The physician positions electrodes 28 within the stomach wall by piercing the wall with needle 20, sliding the electrodes into place, and suturing lead 14 against stomach 24 (90). The physician then cuts retrieval wire 16 proximal to needle 20 to remove the needle from lead 14 (92).

The physician continues implantation by retrieving the proximal end of lead 14 by grabbing retrieval wire 16 with forceps 22 (94). Once retrieval wire 16 is pulled to gain access to connector 38 and connector ring 34, the physician removes the retrieval wire by cutting the wire (96), e.g., with a scissors. The physician then connects lead 14 to an IMD and implants the IMD (98).

In other embodiments, retrieval wire 16 may be removed via other methods. For example, retrieval wire 16 may be pulled with a force that causes the retrieval wire to fracture near the distal end of lead 14. Alternatively, retrieval wire 16 may be attached to the IMD and not removed from lead 14.

In some other embodiments, as mentioned above, lead 14 may be implanted through the use of a laparoscopic technique which may involve multiple trocars inserted into patient 12. In an exemplary laparoscopic procedure, the physician may insert one trocar for a camera, one trocar to retract the liver, and at least two operating ports. One operating port is for left hand use and the other operating port is for right hand use. A larger trocar, e.g., 10 mm in diameter, may be used by the right hand to introduce lead 14 into position. The larger trocar is used to introduce lead 14, pass needle 20 when positioning the electrodes in stomach 24, and withdraw retrieval wire 16 to a pocket for connecting the lead to an IMD.

The procedure continues with the physician retracting the liver if necessary, and then inserting lead 14 into the large trocar. The physician may mark the stomach wall to facilitate electrode placement and insert needle 20 with the aid of a needle holder inserted through the other trocar. Once the electrodes are correctly placed, the physician may use one or more sutures to fix the distal portion of lead 14 in place. The physician next removes needle 20 from lead 14. The physician grasps retrieval wire 16 and pulls the wire through the large trocar to move the proximal end of lead 14 to a pocket created for implantation of an IMD. The laparoscopic technique may limit lead tunneling for lead 14 to reach the IMD. The retrieval wire 16 allows the physician to move lead 14 without possibly damaging lead connectors from a lack of tactile feedback from the trocar.

Figure 7:
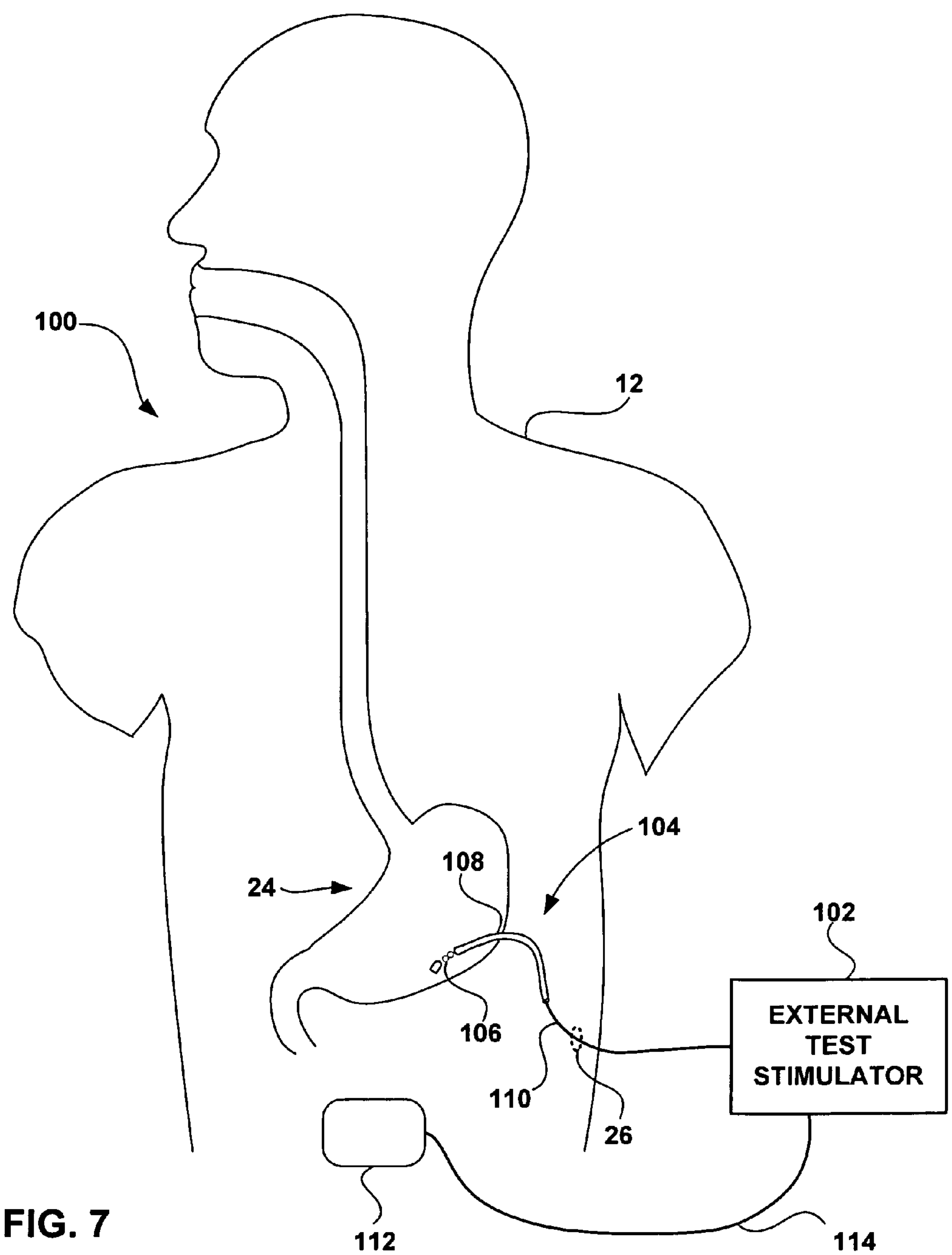
FIG. 7 is a schematic diagram illustrating an implantable medical lead that includes a retrieval wire that allows test stimulation.

FIG. 7 is a schematic diagram illustrating an implantable medical lead that includes a retrieval wire that allows test stimulation. As shown in FIG. 7, system 100 includes medical lead 104 (lead 104), stomach 24, and external test stimulator 102, and ground pad 112. Lead 104 includes retrieval wire 110, flexible lead body 108, and electrodes 106. Lead 104 is tunneled into patient 12 through skin opening 26 created by a physician. The physician uses a forceps (similar to forceps 22 of FIG. 1) to grasp retrieval wire 110 and pull the proximal end of lead body 108 away from stomach 24 and towards the location of external test stimulator 102 (ETS 102). Ground pad 112 is attached to the abdomen of patient 12 and connected to ETS 102 via cable 114. ETS 102 allows the physician to test the placement and stimulation field via retrieval wire 110 during implantation. Lead 104 may be substantially similar to lead 14 of FIG. 1.

Lead 104 includes a proximal end and distal end, where electrodes 106 are located at the distal end and retrieval wire 110 is the proximal end. Electrodes 106 may include one or more electrodes disposed at the distal end of flexible lead body 108. Retrieval wire 110 extends from the proximal end of the lead body. Electrodes 106 may deliver bipolar stimulation to the wall of stomach 24 via retrieval wire 10. Alternatively, one electrode may deliver unipolar stimulation to the wall of stomach via retrieval wire 110 in combination with ground pad electrode 112. Retrieval wire 110 extends from a channel within flexible lead body 108. In this manner, retrieval wire 110 does not increase the diameter of flexible lead body 108, thereby reducing tissue displacement during insertion of lead 104. Retrieval wire 110 may be a continuous filament that is disposed throughout the entire length of flexible lead body 108 and crimped at one or more location along the length of lead body 108.

Once skin opening 26 is created, the physician may insert lead 104 through the opening and tunnel the lead through patient 12 in order to approach the target tissue of stomach 24. An endoscopic camera may be used to facilitate guidance of the lead through patient 12. The physician pierces the wall of stomach 24 with a needle (not shown, similar to needle 20 of FIG. 1) and exits the stomach wall before breaching the inner lining of the stomach. The physician then pulls the distal end of lead body 108 through the wall of stomach 24 until the one or more electrodes at the distal end of lead 104 are positioned within the target tissue of stomach 24. The target tissue of stomach 24 may be smooth muscle that is involved with peristaltic movement of the stomach.

After lead 104 is correctly positioned, the physician may use suture to attach the lead to stomach 24 or other adjacent tissue and remove the needle from the lead. At this point in the implantation procedure, the physician may connect retrieval wire 110 to ETS 102 to test the position of electrodes 106, e.g., via a screw-down terminal, a spring-loaded terminal, or any of a variety of terminals or clips. Retrieval wire 110 may be electrically coupled to one of the electrodes 106 implanted within stomach 24. The physician attaches a ground pad 112 as a return electrode to allow for the test stimulation.

ETS 102 may be programmed by the physician to deliver predetermined test pulses to patient 12. The physician identifies the delivered stimulation and determines if electrodes 106 are properly placed. In some embodiments, ETS 102 may display an electrical field graph to the physician of the test pulses. ETS 102 may be used for a short period of time, generally between a few minutes to a few weeks. Generally, the stimulation is performed under the supervision of the physician. If the physician is not satisfied with the test stimulation, the physician may reposition electrodes 106 in stomach 24. In some embodiments, one or more connectors at the proximal end of lead 104 may be insulated during the test stimulation and removed before chronic use not utilizing retrieval wire 110.

Once test stimulation is complete and successful, the physician may remove ground pad 112 and disconnect ETS 102. The physician then may remove retrieval wire 110 and couple the connectors at the proximal end of lead 14 to an implantable medical device (IMD) not shown in FIG. 7. The physician may remove retrieval wire 110 by cutting the wire next to the proximal end of flexible lead body 108. Other methods of removing retrieval wire 110 may include melting the wire, fracturing the wire, crimping the wire, or any other manner of removing the wire without disturbing the already implanted lead 104. Retrieval wire 110 may be substantially axially stiff to prevent distention of the wire when tensile forces are applied to the wire.

After retrieval wire 110 is removed from flexible lead body 108, the connector may couple lead 104 to an IMD. The IMD may be implanted into a pocket created within patient 12. Alternatively, the IMD may be an external chronic stimulator or external trial stimulator connected to lead 104. The external trial stimulator may provide temporary stimulation therapy to patient 12 in order to evaluate the efficacy of stimulation therapy. If successful, lead 104 may be coupled to an IMD implanted within the patient. In some embodiments, a lead extension may provide a link between lead 104 and the IMD by being coupled to the connector of lead 104 and the IMD. In this case, the lead extension may be removed when implanting a chronic IMD if therapy is successful.

Retrieval wire 110 may be constructed of one or more filaments of an electrically conductive flexible material that retains substantial axial rigidity. The filaments may be preferably constructed of steel, stainless steel, aluminum, titanium, or other metallic alloys. Some combination polymer and metallic filaments may be employed as well. The filaments may be a single filament, multi-filament, or braided to create retrieval wire 16. In some embodiments, retrieval wire 16 may be a tube which allows a structure to be inserted within the tube or a fluid to be delivered to patient 12. The fluid may be a sterile fluid or drug to treat patient 12.

Figure 8:
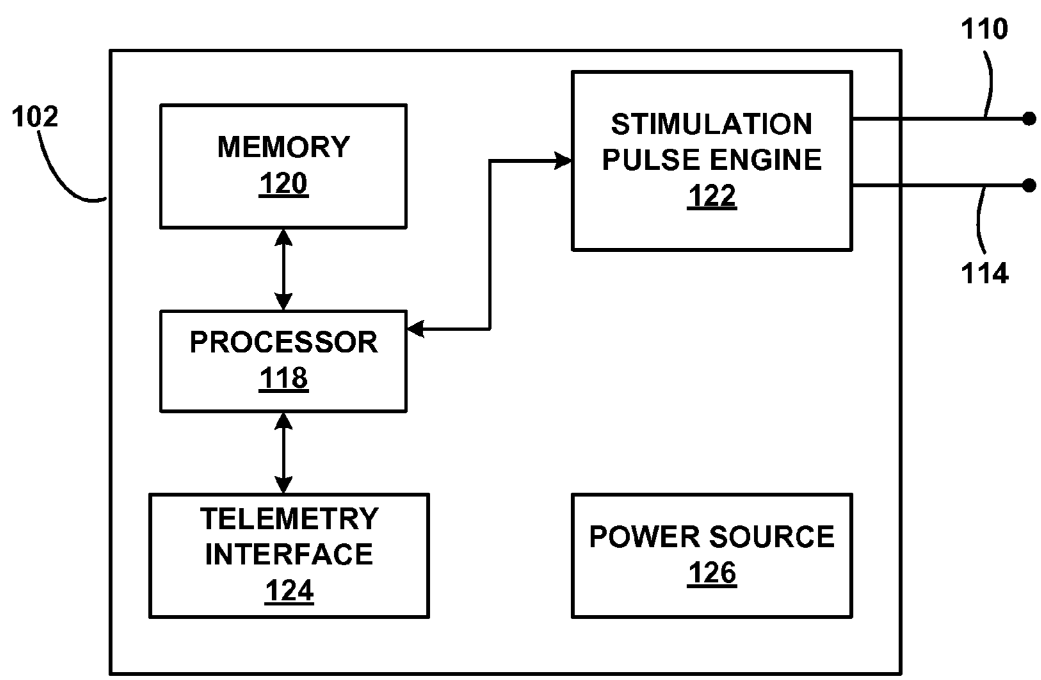
FIG. 8 is a functional block diagram illustrating various components of an exemplary external test stimulator.

FIG. 8 is a functional block diagram illustrating various components of an exemplary external test stimulator. Similar components may be provided in an implantable stimulator used with a lead with a retrieval wire, as described in this disclosure. As shown in FIG. 8, ETS 102 includes processor 118, memory 120, stimulation pulse engine 122, telemetry interface 124, and power source 126. Retrieval wire 110 and cable 114 extend from the housing of ETS 102 and terminate at stomach 24. Memory 120 stores instructions for execution by processor 118, stimulation parameters and, optionally, sense information relating to sensed physiological conditions of patient 12. Memory 120 may include separate memories for storing instructions, stimulation parameter sets, and stimulation information, or a common memory.

For gastric stimulation or other stimulation applications, pulse generator 122 may generally conform to the pulse generator provided in the Enterra Therapy™ Gastric Electrical Stimulation (GES) System, manufactured by Medtronic, Inc. of Minneapolis, Minn. For operation, ETS 102 is programmed with stimulation pulse parameters appropriate for delivery of spike stimulation in the form of stimulation pulses delivered continuously at a rate of approximately 30 to 120 pulses per minute, or delivered as bursts of stimulation pulses at a rate of 2 to 20 bursts per minute to mimic slow wave activity. Within each burst, the pulses may be delivered at a rate of approximately 30 to 120 pulses per minute. However, the test pulses may be modified by the physician as needed to determine the efficacy of positioned electrodes 106.

Processor 118 controls stimulation pulse engine 122 to deliver electrical stimulation therapy. Based on stimulation parameters programmed in memory 120, processor 118 instructs appropriate stimulation by stimulation pulse engine 122. Information may be received from physician at any time during operation via a user interface or telemetry interface 124, in which case a change in stimulation parameters may immediately occur. Processor 118 determines any pulse parameter adjustments based on the received information, and loads the adjustments into memory 120 for use during delivery of stimulation.

Wireless telemetry in ETS 102 may be accomplished by radio frequency (RF) communication or proximal inductive interaction of ETS 102 with another computing device (not shown) via telemetry interface 124. Processor 118 controls telemetry interface 124 to exchange information with the computing device. Processor 118 may transmit operational information and sensed information to programmer 14 via telemetry interface 124. Also, in some embodiments, pulse generator 122 may communicate with other implanted devices, such as stimulators or sensors, via telemetry interface 124 as appropriate to the situation of patient 12. As an alternative or addition to wireless telemetry, ETS 102 may be equipped for communication with other devices via a wired interface. Wireless telemetry typically will be necessary in an IMD, e.g., for communication with an external programmer or controller.

Power source 126 delivers operating power to the components of ETS 102. Power source 126 may include a battery and a power generation circuit to produce the operating power. In some embodiments, the battery may be rechargeable to allow extended operation Recharging may be accomplished through a cable or standard electrical outlet. In some embodiments, ETS 102 may be directly connected to a standard electrical outlet or adapter.

In alternative embodiments, ETS 102 may be a manual pulse generator that is controlled directly by the physician. In this case, ETS 102 may not contain automated features described herein that are similar to an IMD. A simple ETS 102 may be all that is necessary to determine the position of electrodes 106 with retrieval wire 110. In particular, a physician may simply use ETS 102 to deliver one or more pulses to observe patient response and thereby verify proper placement of electrodes 106. For example, the physician may observe an electrical signal indicative of a physiological response to the delivery of a pulse to verify that the electrodes 106 are placed in a position sufficient to effectively target the appropriate region of the stomach.

Figure 9:
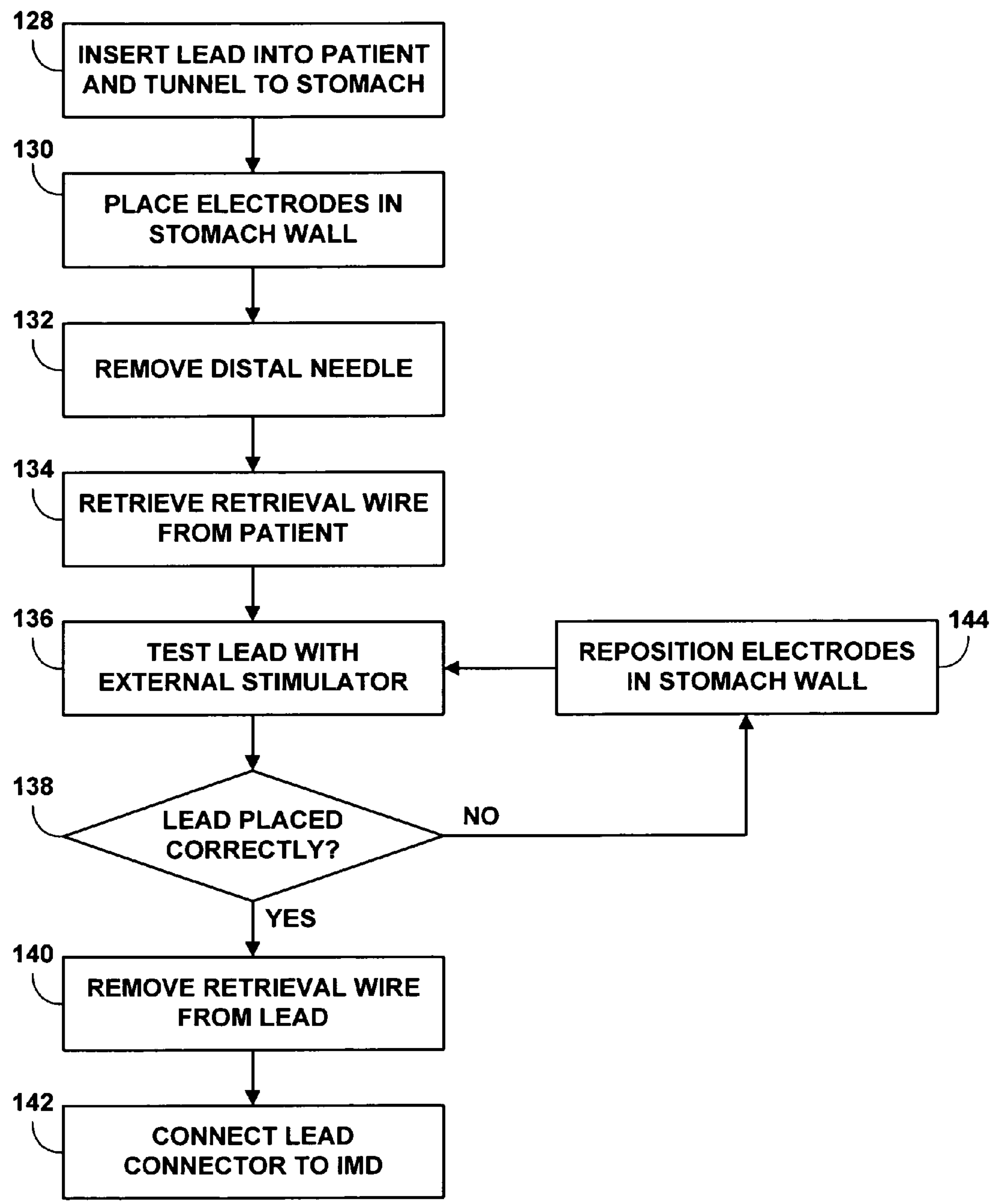
FIG. 9 is a flow chart illustrating a technique for utilizing a retrieval wire during medical lead implantation to test electrode location.

FIG. 9 is a flow chart illustrating a technique for utilizing a retrieval wire during medical lead implantation to test electrode location. As shown in FIG. 9, lead 104 is inserted into opening 26 created in the skin of patient 12 by a physician, and the physician continues by tunneling lead 104 to a target location in the wall of stomach 24 (128). The physician positions electrodes 106 within the stomach wall by piercing the wall with a needle, sliding the electrodes into place, and suturing lead 104 against stomach 24 (130). The physician then cuts retrieval wire 110 proximal to the needle to remove the needle from lead 104 (132).

The physician continues to implantation by retrieving the proximal end of lead 104 by grabbing retrieval wire 110 with a forceps (134). Once retrieval wire 110 is pulled to remove slack from lead 104, the physician connects retrieval wire 110 and ground pad 112 to ETS 102 and tests electrodes 106 position (136). If lead 104 is not placed correctly (138), the physician repositions electrodes 106 (144) before retesting the lead (136). If lead 104 is placed correctly, the physician removes retrieval wire 110 by cutting the wire (140). The physician then connects lead 104 to an IMD and implants the IMD (142). The test stimulation is ideally performed in a short time under the supervision of a physician due to the percutaneous retrieval wire 110.

Although the disclosure generally describes various embodiments of an implantable lead having a retrieval wire, the disclosure further contemplates systems that incorporate such a lead in combination with a stimulation device coupled to the lead, such as an ETS or IMD. Hence, the disclosure contemplates various embodiments including implantable stimulation or sensing leads with retrieval wires, implantable stimulation or sensing systems including one or more implantable leads with retrieval wires in combination with one or more implantable medical devices, such as implantable electrical stimulators, and test stimulation or sensing systems including one or more implantable leads with retrieval wires in combination with one or more external devices, such as external test stimulators.

An IMD, in various embodiments of the described invention, may include processors that are realized by microprocessors, Application-Specific Integrated Circuits (ASIC), Field-Programmable Gate Arrays (FPGA), or other equivalent integrated or discrete logic circuitry. The processor may also utilize several different types of data storage media to store computer-readable instructions for device operation. These memory and storage media types may include any form of computer-readable media such as magnetic or optical tape or disks, solid state volatile or non-volatile memory, including random access memory (RAM), read only memory (ROM), electronically programmable memory (EPROM or EEPROM), or flash memory.

Many embodiments of the invention have been described. Various modifications may be made without departing from the scope of the claims. These and other embodiments are within the scope of the following claims.

The invention claimed is:

1. An assembly comprising:
a medical lead including:
a flexible lead body having a distal end and a proximal end,
one or more electrodes disposed near the distal end of the lead body, and
a lead connector having a proximal end and a distal end, the distal end of the lead connector being engaged to the proximal end of the lead body and including one or more electrical contacts;
a flexible retrieval wire that extends through the lead connector and from the proximal end of the lead connector,
wherein the medical lead is configured to be positioned within a patient with the retrieval wire securely attached to a section of the medical lead to facilitate moving the medical lead, with the retrieval wire securely attached to the section of the medical lead, into a position such that the electrodes are adjacent a target tissue of the patient; and
a needle attached to a distal end of the retrieval wire, wherein the needle allows for lead implantation.

2. The assembly of claim 1, wherein the retrieval wire extends continuously along substantially an entire length of the flexible lead body.

3. The assembly of claim 2, wherein the retrieval wire is crimped at one or more locations within the flexible lead body.

4. The assembly of claim 1, wherein the retrieval wire is attached within a proximal section of the flexible lead body.

5. The assembly of claim 4, wherein the retrieval wire is attached via at least one of crimping, pinching, and tying the retrieval wire within the lead body.

6. The assembly of claim 1, wherein a failure force of the retrieval wire in tension is greater than approximately 2.0 Newtons (N).

7. The assembly of claim 6, wherein the failure force of the retrieval wire in tension is greater than approximately 15.0 N.

8. The assembly of claim 1, wherein a length of at least a portion of the retrieval wire extending from the proximal end of the lead is in a range of approximately 4 to 30 centimeters.

9. The assembly of claim 1, wherein the flexible retrieval wire extends along substantially an entire length of the flexible lead body and extends out from the distal end of the lead body.

10. The assembly of claim 1,
wherein the retrieval wire is constructed of an electrically conductive material,
wherein the electrically conductive material of the retrieval wire extends through the lead connector and from the proximal end of the lead connector,
wherein the electrically conductive material of the retrieval wire is electrically coupled to at least one of the one of more electrodes, and
wherein the medical lead further includes one or more conductors traveling the length of the lead to electrically couple the electrodes to the electrical contacts in the lead connector.

11. The assembly of claim 10, wherein the electrically conductive material is selected from the group consisting of nitinol, titanium, a steel alloy, and an aluminum alloy.

12. A method for implanting a flexible medical lead in a patient, the method comprising:
inserting a distal end of medical lead into a patient, wherein a flexible retrieval wire that is securely attached to a section of the medical lead prior to and during the insertion;
positioning one or more electrodes disposed near the distal end of the medical lead adjacent to a target tissue of the patient while the retrieval wire is securely attached to the section of the lead, wherein the one or more electrodes are electrically coupled to the flexible retrieval wire constructed of an electrically conductive material;
pulling the flexible retrieval wire that extends from a proximal end of a lead connector disposed at a proximal end of the medical lead to access the proximal end of the medical lead, wherein the flexible retrieval wire extends through the lead connector and extends out from the distal end of the medical lead, wherein the lead connector includes one or more electrical contacts; and
delivering test stimulation to the patient via the electrically conductive material of the retrieval wire and the one or more electrodes electrically coupled to the retrieval wire.

13. The method of claim 12, further comprising removing the retrieval wire from the medical lead.

14. The method of claim 13, wherein removing the retrieval wire comprises cutting the retrieval wire near the proximal end of the medical lead.

15. The method of claim 14, wherein removing the retrieval wire comprises cutting the retrieval wire near the distal end of the medical lead to release a needle attached to a distal end of the retrieval wire, wherein the needle allows for lead implantation.

16. The method of claim 13, further comprising coupling the lead connector disposed at the proximal end of the medical lead to an implantable medical device after the retrieval wire is removed.

17. The method of claim 12, wherein the target tissue is at least one of a stomach, a small intestine, and a large intestine of the patient.

18. The method of claim 12, wherein the retrieval wire is crimped at one or more locations within the flexible medical lead.

19. The method of claim 12, wherein the retrieval wire is attached within a proximal section of the flexible medical lead.

20. The method of claim 12, wherein the retrieval wire is constructed of an electrically conductive material.

21. The method of claim 20, wherein the electrically conductive material is selected from the group consisting of nitinol, titanium, a steel alloy, and an aluminum alloy.

22. The method of claim 12, wherein a failure force of the retrieval wire in tension is greater than approximately 2.0 Newtons (N).

23. The method of claim 12, wherein the failure force of the retrieval wire in tension is greater than approximately 15.0 Newtons.

24. The method of claim 12, further comprising delivering stimulation via the one or more electrodes to a portion of the gastrointestinal track.

25. The method of claim 12, wherein a length of at least a portion of the retrieval wire extending from the proximal end of the lead is in a range of approximately 4 to 30 centimeters.

26. An implantable stimulation system comprising:

an electrical stimulator;

an implantable lead coupled to the electrical stimulator, wherein the lead includes a flexible lead body having a distal end and a proximal end, and one or more electrodes disposed near the distal end of the lead body;

a lead connector having a proximal end, the lead connector located on the proximal end of the lead body, and including one or more electrical contacts;

a flexible retrieval wire that extends along substantially an entire length of the flexible lead body, extends from the proximal end of the lead connector and extends out from the distal end of the lead body and is detachable from the lead body for coupling of the connector to the electrical stimulator; and a needle attached to a distal end of the retrieval wire, wherein the needle allows for lead implantation, wherein the implantable lead is configured to be positioned within a patient with the retrieval wire securely attached to a section of the implantable lead to facilitate moving the implantable lead, with the retrieval wire securely attached to the section of the implantable lead, into a position such that the electrodes are adjacent a target tissue of the patient.

27. The system of claim 26, wherein the retrieval wire is crimped at one or more locations within the flexible lead body.

28. The system of claim 26, wherein a failure force of the retrieval wire in tension is greater than approximately 15.0 Newtons.

29. The system of claim 26, wherein a length of at least a portion of the retrieval wire extending from the proximal end of the lead is in a range of approximately 4 to 30 centimeters.

30. The system of claim 26, wherein the electrical stimulator is at least one of an implantable chronic stimulator, an external chronic stimulator, and an external trial stimulator.

31. The system of claim 26, wherein the retrieval wire is constructed of an electrically conductive material, wherein the electrically conductive material of the retrieval wire extends through the lead connector and from the proximal end of the lead connector, wherein the electrically conductive material of the retrieval wire is electrically coupled to at least one of the one of more electrodes, and wherein the implantable lead further includes one or more conductors traveling the length of the lead to electrically couple the electrodes to the electrical contacts in the lead connector.

* * * * *